(12) United States Patent
Hinayama et al.

(10) Patent No.: US 11,136,420 B2
(45) Date of Patent: Oct. 5, 2021

(54) WATER-ABSORBENT RESIN AND METHOD OF PRODUCING WATER-ABSORBENT RESIN

(71) Applicant: Sumitomo Seika Chemicals Co. Ltd., Kako-gun (JP)

(72) Inventors: Tetsuhiro Hinayama, Himeji (JP);
Masahiro Murakami, Himeji (JP);
Hiroki Yabuguchi, Himeji (JP); Hideki Yokoyama, Himeji (JP)

(73) Assignee: Sumitomo Seika Chemicals Co. Ltd., Kako-gun (JP)

( * ) Notice: Subject to any disclaimer, the term of this patent is extended or adjusted under 35 U.S.C. 154(b) by 0 days.

(21) Appl. No.: 16/804,095

(22) Filed: Feb. 28, 2020

(65) Prior Publication Data

US 2020/0199263 A1      Jun. 25, 2020

Related U.S. Application Data

(62) Division of application No. 15/324,753, filed as application No. PCT/JP2014/079242 on Nov. 4, 2014, now abandoned.

(30) Foreign Application Priority Data

Jul. 11, 2014  (JP) .................................. 2014-143714
Oct. 31, 2014  (JP) .................................. 2014-223721

(51) Int. Cl.
 *C08F 8/14*  (2006.01)
 *C08F 2/32*  (2006.01)
 (Continued)

(52) U.S. Cl.
 CPC ................ *C08F 8/14* (2013.01); *A61F 13/15* (2013.01); *A61F 13/49* (2013.01); *A61F 13/53* (2013.01);
(Continued)

(58) Field of Classification Search
USPC .............................................. 526/219.2, 930
See application file for complete search history.

(56) References Cited

U.S. PATENT DOCUMENTS

| 5,180,798 A | 1/1993 | Nakamura et al. |
| 5,562,646 A | 10/1996 | Goldman et al. |

(Continued)

FOREIGN PATENT DOCUMENTS

| AU | 2008289997 A1 | 2/2009 |
| CN | 102875944 A | 1/2013 |

(Continued)

OTHER PUBLICATIONS

Notice of Reasons for Rejection dated Dec. 2, 2014, issued to JP Application No. 2014-223721 and machine English translation thereof.

(Continued)

*Primary Examiner* — Fred M Teskin
(74) *Attorney, Agent, or Firm* — Locke Lord LLP; James E. Armstrong, IV; Nicholas J. DiCeglie, Jr.

(57) ABSTRACT

Provided is a method of producing a water-absorbent resin comprising a step of polymerizing a water-soluble ethylenically unsaturated monomer in the presence of an internal-crosslinking agent, and a step of performing post-crosslinking, wherein:
 the step of polymerizing comprises one or more polymerization steps;
 all the polymerization steps are performed in the presence of both one or more azo based compounds and peroxides so that the both are coexistent in the all steps;
 in each polymerization step, a proportion of the azo compounds is 40-95 mass % relative to an amount of the azo compounds and the peroxides;
(Continued)

the water-absorbent resin has a water-absorption capacity of physiological saline under a load of 4.14 kPa at 120 minutes passed from the start of water absorption of 20 ml/g or more; and the degree of swelling under a load at 30 minutes is 70%.

2 Claims, 1 Drawing Sheet

(51) Int. Cl.

| | | |
|---|---|---|
| *A61F 13/49* | (2006.01) | |
| *A61F 13/53* | (2006.01) | |
| *A61F 13/15* | (2006.01) | |
| *A61L 15/24* | (2006.01) | |
| *A61L 15/60* | (2006.01) | |
| *B01J 20/26* | (2006.01) | |

(52) U.S. Cl.
CPC .............. *A61L 15/24* (2013.01); *A61L 15/60* (2013.01); *B01J 20/267* (2013.01); *C08F 2/32* (2013.01)

(56) References Cited

U.S. PATENT DOCUMENTS

| | | | |
|---|---|---|---|
| 5,624,967 A | 4/1997 | Hitomi et al. | |
| 5,760,080 A | 6/1998 | Wada et al. | |
| 6,150,582 A | 11/2000 | Wada et al. | |
| 8,252,715 B2 | 8/2012 | Torii et al. | |
| 8,846,823 B2 | 9/2014 | Nakamura et al. | |
| 9,187,579 B2 | 11/2015 | Ikeuchi et al. | |
| 9,669,386 B2 | 6/2017 | Wada et al. | |
| 10,323,105 B2 * | 6/2019 | Yabuguchi ................ C08F 8/00 | |
| 2005/0059762 A1 | 3/2005 | Jonas et al. | |
| 2008/0032888 A1 | 2/2008 | Nakamura et al. | |
| 2008/0221229 A1 | 9/2008 | Torii et al. | |
| 2009/0215617 A1 | 8/2009 | Kimura et al. | |
| 2010/0009846 A1 | 1/2010 | Ikeuchi et al. | |
| 2013/0175473 A1 | 7/2013 | Wada et al. | |
| 2013/0330566 A1 | 12/2013 | Takatori | |
| 2014/0031203 A1 | 1/2014 | Kondo et al. | |
| 2014/0194574 A1 | 7/2014 | Handa et al. | |
| 2015/0216740 A1 | 8/2015 | Watanabe et al. | |

FOREIGN PATENT DOCUMENTS

| | | |
|---|---|---|
| CN | 103153455 A | 6/2013 |
| EP | 0288865 A2 | 11/1988 |
| EP | 0349240 | 4/1997 |
| EP | 1072630 A1 | 1/2001 |
| EP | 0629411 | 10/2001 |
| EP | 1358892 A1 | 11/2003 |
| EP | 1637105 A1 | 3/2006 |
| EP | 0872491 B1 | 5/2006 |
| EP | 1882701 A1 | 1/2008 |
| EP | 1765913 B1 | 8/2008 |
| EP | 2116571 A1 | 11/2009 |
| EP | 2127741 A1 | 12/2009 |
| EP | 2184300 A1 | 5/2010 |
| EP | 2623198 A1 | 8/2013 |
| EP | 2700659 A1 | 2/2014 |
| EP | 2891520 A1 | 7/2015 |
| EP | 2893974 A1 | 7/2015 |
| JP | 03-227301 A | 10/1991 |
| JP | H05-078420 A | 3/1993 |
| JP | 06-287233 A | 10/1994 |
| JP | 06-345819 A | 12/1994 |
| JP | H08-057310 A | 3/1996 |
| JP | H08-057311 A | 3/1996 |
| JP | 08-120013 A | 5/1996 |
| JP | H08-188602 A | 7/1996 |
| JP | 09-124710 A | 5/1997 |
| JP | H09-194514 A | 7/1997 |
| JP | H09-510889 A | 11/1997 |
| JP | H11-029605 A | 2/1999 |
| JP | H11-058615 A | 3/1999 |
| JP | H11-080248 A | 3/1999 |
| JP | 11-335404 A | 12/1999 |
| JP | 2002-179712 A | 6/2002 |
| JP | 2002-212331 A | 7/2002 |
| JP | 2003-088551 A | 3/2003 |
| JP | 2003-516431 A | 5/2003 |
| JP | 2004-261796 A | 9/2004 |
| JP | 2005-344103 A | 12/2005 |
| JP | 2006-176570 A | 7/2006 |
| JP | 2008-007567 A | 1/2008 |
| JP | 2008-133396 A | 6/2008 |
| JP | 2008-280459 A | 11/2008 |
| JP | 2009-019065 A | 1/2009 |
| JP | 2009-509723 A | 3/2009 |
| JP | 2009-510177 A | 3/2009 |
| JP | 2009-280668 A | 12/2009 |
| JP | 2012-041439 A | 3/2012 |
| JP | 2012-236898 A | 12/2012 |
| KR | 10 2001 0087042 A | 9/2001 |
| WO | 01/41818 A1 | 6/2001 |
| WO | 01/42339 A1 | 6/2001 |
| WO | 2004/069936 A1 | 8/2004 |
| WO | 2004/110328 A1 | 12/2004 |
| WO | 2005/027987 A1 | 3/2005 |
| WO | 2005/097313 A1 | 10/2005 |
| WO | 2005/108472 A1 | 11/2005 |
| WO | 2006/014031 A1 | 2/2006 |
| WO | 2007/037453 A1 | 4/2007 |
| WO | 2008/096713 A1 | 8/2008 |
| WO | 2008/108343 A1 | 9/2008 |
| WO | 2009/150984 A1 | 12/2009 |
| WO | 2012/043821 A1 | 4/2012 |
| WO | 2012/132902 A1 | 10/2012 |
| WO | 2012/144564 A1 | 10/2012 |
| WO | 2014/038324 A1 | 3/2014 |
| WO | 2014/079710 A1 | 5/2014 |

OTHER PUBLICATIONS

Notice of Reasons for Rejection dated Jan. 27, 2015, issued to JP Application No. 2014-223721 and machine English translation thereof.
International Search Report dated Dec. 2, 2014, issued for PCT/JP2014/079242.
Experimental result report (Kou-2) dated Aug. 10, 2016, by Katada and English translation thereof.
Experimental result report (Kou-4) dated Aug. 10, 2016, by Katada and English translation thereof.
"Polymer Analysis and Network Structure," Modern Superabsorbent Polymer Technology (1998), p. 155, p. 159-160, pp. 201-213.
Written Opposition dated Oct. 19, 2016, issued for Japanese Patent No. 5893116 and English translation thereof.
Supplementary Search Report dated Apr. 3, 2017, issued for European Patent Application No. 14897178.1.
Office Action dated Jul. 7, 2017, issued for EP Patent Application No. 14897178.1.
Office Action dated Apr. 4, 2018, issued to EP Patent Application No. 14897178.1.
Office Action dated Dec. 5, 2018, issued in the EP Patent Application No. EP14897178.1.
Notification of Reasons for Refusal issued in the JP Patent Application No. 2014-223721, dated Oct. 20, 2015.
Office Action issued in the ID Patent Application No. IDP00201609110, dated Jul. 19, 2019.
Examination Report issued in corresponding Indian Patent Application No. IN 201717000216, dated Dec. 19, 2019.
Office Action issued in the EP Patent Application No. EP14897322.5, dated Dec. 5, 2018.
Office Action issued in the CN Application No. CN201480080354.X, dated Jul. 30, 2018.
Final Action issued in the U.S. Appl. No. 15/324,764, dated Aug. 14, 2018.

(56) References Cited

OTHER PUBLICATIONS

Office Action issued in the EP Patent Application No. EP14897322.5, dated Mar. 19, 2018.
Office Action issued in the U.S. Appl. No. 15/324,764, dated Jan. 16, 2018.
Supplementary Search Report issued in the EP Patent Application No. EP14897322.5 dated Mar. 17, 2017.
Experimental result report (Kou 2-1) (Discussion in Written Opposition for Japanese Patent No. 5893117 dated Oct. 19, 2016).
Experimental result report (Kou 2-2).
Experimental result report (Kou 4) (Discussion in Written Opposition for Japanese Patent No. 5893117 dated Oct. 19, 2016).
Experimental result report (Kou 7).
Written Opposition for Japanese Patent No. 5893117 dated Oct. 19, 2016.
Notice of Reasons for Rejection issued in the JP Application No. 2014-223722, dated Dec. 2, 2014.
International Search Report including Written Opinion issued in the International Application No. PCT/JP2014/079243 dated Nov. 2, 2014.
Office Action issued in the IN Patent Application No. IN201717000212, dated Nov. 28, 2019.
Description of Reproduction Experiments relating to Examples 1 and 6 and Comparative Example 10 of EP2623198A1 (Presented in Notice of Opposition dated May 8, 2020 issued for EP Patent No. 3153529).
Description of Reproduction Experiment relating to Example 10 of EP1072630A1 (Presented in Notice of Opposition dated May 8, 2020 issued for EP Patent No. 3153529).
Description of Reproduction Experiment relating to Example 3 of EP1358892A1 (Presented in Notice of Opposition dated May 8, 2020 issued for EP Patent No. 3153529).
Description of Reproduction Experiment relating to Example 4 of EP2891520A1 (Presented in Notice of Opposition dated May 8, 2020 issued for EP Patent No. 3153529).
Description of Reproduction Experiment relating to Example 2 of WO2006/014031A1 (Presented in Notice of Opposition dated May 8, 2020 issued for EP Patent No. 3153529).
Description of Reproduction Experiment relating to Example 5 of JPH11-080248A (Presented in Notice of Opposition dated May 8, 2020 issued for EP Patent No. 3153529).
Description of Reproduction Experiment relating to Example 2 of EP0349240A2 (Presented in Notice of Opposition dated May 8, 2020 issued for EP Patent No. 3153529).
Buchholz, F. L. (Ed.) et al., Modern Superabsorbent Polymer Technology, pp. 69-117, 1998.
Comparison of SAP properties—opposed patent, EP2893974A1, EP1882701A1, JP2012-236898A and JP2008-133396A (Presented in Notice of Opposition dated May 8, 2020 issued for EP Patent No. 3153529).
Description of Reproduction Experiment relating to Example 19 of JP2005-344103A (Presented in Notice of Opposition dated May 8, 2020 issued for EP Patent No. 3153529).
Comparison of SAP properties—opposed patent, EP0288865A2 and WO2014/079710A1 (Presented in Notice of Opposition dated May 8, 2020 issued for EP Patent No. 3153529).
Communication of a Notice of Opposition dated May 8, 2020 issued for EP Patent No. 3153529 (Application No. EP14897322.5).
Brief communication dated Feb. 4, 2021 enclosing a letter from Opponent issued for EP Patent No. 3153529 (Application No. EP14897322.5).
Summons to attend oral proceedings issued for EP Patent No. 3153529 dated Feb. 9, 2021 (Application No. EP14897322.5).

\* cited by examiner

WATER-ABSORBENT RESIN AND METHOD OF PRODUCING WATER-ABSORBENT RESIN

CROSS REFERENCE TO RELATED APPLICATIONS

This Application is a Divisional of U.S. patent application Ser. No. 15/324,753 filed on Jan. 9, 2017, which Application is the National Phase under 35 U.S.C. § 371 of PCT International Application No. PCT/JP2014/079242, filed Nov. 4, 2014, which application claims priority to Japanese Patent Application Nos. JP 2014-223721 filed on Oct. 31, 2014, and Japanese Patent Application No. JP 2014-143714 filed on Jul. 11, 2014. The entire contents of these applications are incorporated herein by reference in their entirety.

This Application is also related to U.S. Pat. No. 10,323,105, filed on Jan. 9, 2017 and issued on Jul. 18, 2009, and U.S. Pat. No. 10,525,443, filed on Jan. 9, 2017 and issued on Jan. 7, 2020; which patents are assigned to the assignee of the present application and are incorporated by reference herein.

TECHNICAL FIELD

The present invention relates to a water-absorbent resin and a method of producing the water-absorbent resin. More specifically, the present invention relates to a water-absorbent resin comprising an absorbent material suitably used for hygienic materials such as disposable diapers, sanitary napkins and incontinence pads, and also relates to a method of producing such the water-absorbent resin.

BACKGROUND ART

In recent years, water-absorbent resins have been widely used in the field of hygienic materials such as disposable diapers, sanitary napkins and incontinence pads.

For water-absorbent resins as described above, cross-linked products of partially neutralized polymers of acrylic acid salt are preferred because they have many advantages, including the followings: they have better water absorption performance; their raw materials such as acrylic acid are easily and industrially available, and therefore they can be produced with stable quality and low cost; and they are more resistant to decomposition and deterioration.

Preferred properties of water-absorbent resins for hygienic materials such as sanitary napkins and disposable diapers include a high water-retention capacity, a better water-absorption rate, a high water-absorption capacity under a load and the like. However, for example, since the water-retention capacity and the water-absorption rate are in a contradictory relationship with the water-absorption capacity under a load, it is difficult to satisfy a balance between these properties.

As technologies to improve the above properties suitably used for hygienic materials, the followings are known: for example, a method of performing reversed phase suspension polymerization using a specific amount of specific macromolecular protective colloid and surfactant (see Patent Document 1); a method of performing reversed phase suspension polymerization in two or more steps (see Patent Document 2); a method of performing reversed phase suspension polymerization in the presence of β-1,3-glucans to obtain a water-absorbent resin and further performing a cross-linking reaction by adding a cross-linking agent to the water-absorbent resin obtained (see Patent Document 3); a method of performing reversed phase suspension polymerization using a specific amount of persulfate (see Patent Document 4); a method of performing aqueous polymerization in the presence of phosphorous acid and/or a salt thereof to obtain a water-absorbent resin precursor, and then mixing the water-absorbent resin precursor with a surface cross-linking agent followed by heating (see Patent Document 5).

However, water-absorbent resins obtained by these methods do not necessarily satisfy those properties such as the high water-retention capacity, the high water-absorption capacity under a load and the better water-absorption rate as described above, and a room for improvement still remains.

Further, when a water-absorbent resin showing a relatively rapid water-absorption rate is used in an absorbent material comprising a water-absorbent resin, the water-absorbent resin may locally absorb a to-be-absorbed liquid around a feeding position of the to-be-absorbed liquid, and the liquid is often blocked because the water-absorbent resin becomes swollen and denser. Moreover, in this case, since the diffusibility of the to-be-absorbed liquid into the absorbent material is prevented by the gelatinized water-absorbent resin, and the to-be-absorbed liquid may not be easily distributed throughout the absorbent material, the amount of re-wet of the to-be-absorbed liquid tends to be larger.

PRIOR ART DOCUMENT

Patent Documents

Patent Document 1: Japanese Unexamined Patent Application Publication No. H06-345819
Patent Document 2: Japanese Unexamined Patent Application Publication No. H03-227301
Patent Document 3: Japanese Unexamined Patent Application Publication No. H08-120013
Patent Document 4: Japanese Unexamined Patent Application Publication No. H06-287233
Patent Document 5: Japanese Unexamined Patent Application Publication No. H09-124710

DISCLOSURE OF THE INVENTION

Problems to be Solved by the Invention

The present invention is proposed in view of these actual circumstances as described above. An objective of the present invention is to provide a water-absorbent resin capable of improving the diffusibility of a to-be-absorbed liquid to effectively reduce the amount of re-wet when used for an absorbent material. Another objective of the present invention is to provide a method of producing the above water-absorbent resin.

Means for Solving the Problems

The present inventors conducted extensive studies in order to solve the problems described above. As a result, the present inventors have found that a water-absorbent resin obtained by polymerizing a water-soluble ethylenically unsaturated monomer in the presence of an internal-cross-linking agent, in which the water-absorption capacity of physiological saline under a load of 4.14 kPa at 120 minutes passed from the start of water absorption is 20 ml/g or more, and the degree of swelling under a load at 30 minutes is 70% or less when the water-absorption capacity of physiological saline under a load of 4.14 kPa at 120 minutes passed from the start of water absorption is taken as a degree of swelling under a load of 100% can increase the diffusibility of a to-be-absorbed liquid in an absorbent material when used in the absorbent material, enabling effective reduction of the amount of re-wet. Further, the present inventors have found that these water-absorbent resins described above can be obtained by a producing method in which reversed phase suspension polymerization of a water-soluble ethylenically unsaturated monomer is performed in a hydrocarbon dispersion medium, the method comprising performing polymerization in the presence of an azo based compound and a peroxide. That is, the present invention provides the followings.

(1) The present invention provides a method of producing a water-absorbent resin by performing reversed phase suspension polymerization of a water-soluble ethylenically unsaturated monomer in the presence of an internal-crosslinking agent in a hydrocarbon dispersion medium, the method comprising the steps of: performing polymerization step in the presence of an azo based compound and a peroxide; and performing post-crosslinking step of a hydrous gel-like material obtained from the polymerization using a post-crosslinking agent.

(2) The invention also provides the method of producing a water-absorbent resin according to (1), wherein the azo based compound is at least one selected from the group consisting of 2,2'-azobis(2-amidinopropane)dihydrochloride, 2,2'-azobis{2-[1-(2-hydroxyethyl)-2-imidazoline 2-yl]propane}dihydrochloride and 2,2'-azobis[N-(2-carboxyethyl)-2-methylpropioneamidine]tetrahydrate.

(3) The present invention also provides the method of producing a water-absorbent resin according to (1) or (2), wherein the peroxide is at least one selected from the group consisting of potassium persulfate, ammonium persulfate, sodium persulfate and hydrogen peroxide.

(4) The present invention also provides the method of producing a water-absorbent resin according to any one of (1) to (3), wherein the internal-crosslinking agent is at least one selected from the group consisting of (poly)ethylene glycol diglycidyl ether, (poly)propylene glycol diglycidyl ether and (poly)glycerin diglycidyl ether.

(5) The present invention provides a water-absorbent resin obtained by performing polymerization of a water-soluble ethylenically unsaturated monomer in the presence of an internal-crosslinking agent, and performing post-crosslinking using a post-crosslinking agent, wherein the water-absorption capacity of physiological saline under a load of 4.14 kPa at 120 minutes passed from the start of water absorption is 20 ml/g or more, and the degree of swelling under a load at 30 minutes is 70% or less when the water-absorption capacity of physiological saline under a load of 4.14 kPa at 120 minutes passed from the start of water absorption is taken as a degree of swelling under a load of 100%. Note that the degree of swelling under a load at a certain time passed is calculated by the following formula:

$$\text{Degree of swelling under a load at a certain time passed (\%)} = \frac{\text{Water absorption capacity for physiological saline under a load of 4.14 kPa at a certain time passed (ml/g)}}{\text{Water absorption capacity for physiological saline under a load of 4.14 kPa at 120 minutes passed (ml/g)}} \times 100$$

[Formula 1]

(6) The present invention also provides an absorbent article using an absorbent material comprising the water-absorbent resin according to (5).

Effects of the Invention

The present invention can provide a water-absorbent resin in which the diffusibility of a to-be-absorbed liquid can be improved to effectively reduce the amount of re-wet when used for an absorbent material.

PREFERRED MODE FOR CARRYING OUT THE INVENTION

The present invention will be described in detail below.

1. Method of Producing Water-Absorbent Resin

The method of producing a water-absorbent resin according to the present invention is a method of performing reversed phase suspension polymerization of a water-soluble ethylenically unsaturated monomer in a hydrocarbon dispersion medium in the presence of an internal-crosslinking agent, characterized by comprising the steps of: performing polymerization step in the presence of an azo based compound and a peroxide; and performing post-crosslinking step of a hydrous gel-like material obtained from the polymerization using a post-crosslinking agent.

<Polymerization Step>
[Water-Soluble Ethylenically Unsaturated Monomer]

Water-soluble ethylenically unsaturated monomers include, for example, (meth)acrylic acid ("(meth)acry" herein refers to both "acry" and "methacry". The same shall apply hereinafter) and salts thereof; 2-(meth)acrylamide-2-methylpropanesulfonic acid and salts thereof; nonionic monomers such as (meth)acrylamide, N,N-dimethyl(meth)acrylamide, 2-hydroxyethyl(meth)acrylate, N-methylol (meth)acrylamide, polyethylene glycol mono(meth)acrylate; amino group-containing unsaturated monomers such as N,N-diethylaminoethyl(meth)acrylate, N,N-diethylaminopropyl(meth)acrylate, diethylaminopropyl(meth)acrylamide and quaternary compounds thereof. Among these water-soluble ethylenically unsaturated monomers, (meth)acrylic acid or salts thereof, (meth)acrylamide, N,N-dimethylacrylamide are preferred in view of easy industrial availability, and (meth)acrylic acid and salts thereof are more preferred. Note that these water-soluble ethylenically unsaturated monomers may be used alone or in combination of two or more.

Among these, acrylic acid and salts thereof are widely used as raw materials for water-absorbent resins, and those materials may be used in which the aforementioned other water-soluble ethylenically unsaturated monomers are copolymerized with these partially neutralized acrylates. In this case, a partially neutralized acrylate is preferably used as a main water-soluble ethylenically unsaturated monomer in an amount of 70 to 100 mol % relative to the total amount of water-soluble ethylenically unsaturated monomers.

A water-soluble ethylenically unsaturated monomer is preferably dispersed in a hydrocarbon dispersion medium in the state of an aqueous solution, and subjected to reversed phase suspension polymerization. A water-soluble ethylenically unsaturated monomer in the form of an aqueous solution can increase the dispersion efficiency in a hydrocarbon dispersion medium. The concentration of a water-soluble ethylenically unsaturated monomer in the aqueous solution is preferably in a range from 20 mass % to the saturation concentration. Further, the concentration of a water-soluble ethylenically unsaturated monomer is more preferably 55 mass % or less, further preferably 50 mass % or less and further more preferably 45 mass % or less. On the other hand, the concentration of a water-soluble ethylenically unsaturated monomer is more preferably 25 mass % or more, further preferably 28 mass % or more, and further more preferably 30 mass % or more.

When a water-soluble ethylenically unsaturated monomer has an acid group such as (meth)acrylic acid, 2-(meth)acrylamide-2-methylpropanesulfonic acid, those having the acid group pre-neutralized with an alkaline neutralizer may be used, if desired. Such alkaline neutralizers include alkali metal salts such as sodium hydroxide, sodium carbonate, sodium hydrogen carbonate, potassium hydroxide, potassium carbonate; ammonia and the like. Further, these alkaline neutralizers may be used in the form of an aqueous solution in order to simply neutralization procedures. Note that the aforementioned alkaline neutralizers may be used alone or in combination of two or more.

For the degree of neutralization of a water-soluble ethylenically unsaturated monomer with an alkaline neutralizer, the degree of neutralization of all acid groups in the water-soluble ethylenically unsaturated monomer is preferably 10 to 100 mol %, more preferably 30 to 90 mol %, further preferably 40 to 85 mol % and further more preferably 50 to 80 mol %.

[Hydrocarbon Dispersion Media]

Hydrocarbon dispersion media include, for example, aliphatic hydrocarbons having 6 to 8 carbon atoms such as n-hexane, n-heptane, 2-methylhexane, 3-methylhexane, 2,3-dimethylpentane, 3-ethylpentane, n-octane; alicyclic hydrocarbons such as cyclohexane, methylcyclohexane, cyclopentane, methylcyclopentane, trans-1,2-dimethylcyclopentane, cis-1,3-dimethylcyclopentane, trans-1,3-dimethylcyclopentane; aromatic hydrocarbons such as benzene, toluene, xylene and the like. Among these hydrocarbon dispersion media, in particular, n-hexane, n-heptane, cyclohexane are suitably used in view of easy industrial availability, stable quality and low cost. These hydrocarbon dispersion media may be used alone or in combination of two or more. Note that examples of a mixture of hydrocarbon dispersion media include commercially available products such as EXXSOL heptane (made by ExxonMobil Corporation: 75 to 85 mass % of heptane and its isomeric hydrocarbons thereof are contained), which can also produce a suitable result.

The used amount of the hydrocarbon dispersion medium is preferably 100 to 1500 parts by mass relative to 100 parts by mass of a first-step water-soluble ethylenically unsaturated monomer, and more preferably 200 to 1400 parts by mass. Note that as described below, reversed phase suspension polymerization is performed in one step (single step) or in multiple steps such as two or more steps, and the first-step polymerization described above means a polymerization reaction of the first step in single-step polymerization or multiple-step polymerization (The same shall apply hereinafter).

[Dispersion Stabilizer]

A dispersion stabilizer may be used in reversed phase suspension polymerization in order to improve the dispersion stability of a water-soluble ethylenically unsaturated monomer in a hydrocarbon dispersion medium.

(Surfactant)

A surfactant can be used as the dispersion stabilizer. As surfactants, the followings may be used: for example, sucrose fatty acid ester, polyglycerin fatty acid, sorbitan fatty acid ester, polyoxyethylene sorbitan fatty acid ester, polyoxyethylene glycerine fatty acid ester, sorbitol fatty acid ester, polyoxyethylene sorbitol fatty acid ester, polyoxyethylene alkyl ether, polyoxyethylene alkyl phenyl ether, polyoxyethylene castor oil, polyoxyethylene hydrogenated castor oil, alkyl allyl formaldehyde condensed polyoxyethylene ether, polyoxyethylene polyoxypropylene block copolymer, polyoxyethylene polyoxy propyl alkyl ether, polyethylene glycol fatty acid ester, alkyl glucoside, N-alkyl gluconamide, polyoxyethylene fatty acid amide, polyoxyethylene alkylamine, phosphate ester of polyoxyethylene alkyl ether, phosphate ester of polyoxyethylene alkyl aryl ether and the like. Among these surfactants, in particular, sorbitan fatty acid ester, polyglycerin fatty acid ester, and sucrose fatty acid ester are preferably used in view of dispersion stability of monomers. These surfactants may be used alone or in combination of two or more.

The used amount of the surfactant is preferably 0.1 to 30 parts by mass relative to 100 parts by mass of a first-step water-soluble ethylenically unsaturated monomer, and more preferably 0.3 to 20 parts by mass.

(Polymeric Dispersion Agent)

Further, a polymeric dispersion agent may also be used, along with a surfactant described above, as a dispersion stabilizer. Polymeric dispersion agents include, for example, maleic anhydride modified polyethylene, maleic anhydride modified polypropylene, maleic anhydride modified ethylene-propylene copolymer, maleic anhydride modified EPDM (ethylene-propylene-diene-terpolymer), maleic anhydride modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylate copolymer, ethyl cellulose, ethyl hydroxyethyl cellulose and the like. Among these polymeric dispersion agents, particularly in view of dispersion stability of monomers, maleic anhydride modified polyethylene, maleic anhydride modified polypropylene, maleic anhydride modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, oxidized ethylene-propylene copolymer are preferably used. These polymeric dispersion agents may be used alone or in combination of two or more.

The used amount of the polymeric dispersion agent is preferably 0.1 to 30 parts by mass relative to 100 parts by mass of a first-step water-soluble ethylenically unsaturated monomer, and more preferably 0.3 to 20 parts by mass.

[Internal-Crosslinking Agent]

The internal-crosslinking agents include, for example, unsaturated polyesters obtained by allowing polyols, for example, diols and triols such as (poly)ethylene glycol ("(poly)" means that the prefix "poly" is optional. The same shall apply hereinafter.), (poly)propylene glycol, 1,4-butanediol, trimethylolpropane, (poly)glycerin to react with unsaturated acids such as (meth)acrylic acid, maleic acid, fumaric acid; bisacrylamides such as N,N-methylenebisacrylamide; di(meth)acrylic acid esters or tri(meth)acrylic acid esters obtained by allowing polyepoxide to react with (meth)acrylic acid; di(meth)acrylic acid carbamyl esters obtained by allowing polyisocyanate such as tolylene diisocyanate, hexamethylene diisocyanate to react with (meth) acrylic acid hydroxyethyl; compounds having two or more polymerizable unsaturated groups, for example, allylated starch, allylated cellulose, diallyl phthalate, N,N',N'''-triallylisocyanate, divinylbenzene and the like; polyglycidyl compounds, for example, diglycidyl compounds such as (poly) ethylene glycol diglycidyl ether, (poly)propylene glycol diglycidyl ether, (poly)glycerin diglycidyl ether, triglycidyl compounds and the like; epihalohydrin compounds such as epichlorohydrin, epibromhydrin, α-methyl epichlorohydrin; compounds having two or more reactive functional groups, for example, isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol. Among these internal-crosslinking agents, polyglycidyl compounds is preferably used, and diglycidyl compounds are more preferably used, and (poly)ethylene glycol diglycidyl ether, (poly)propylene glycol diglycidyl ether, (poly)glycerin diglycidyl ether are further preferably used. These internal-crosslinking agents may be used alone or in combination of two or more.

The used amount of the internal-crosslinking agent is preferably 0.000001 to 0.02 mol relative to 1 mol of a water-soluble ethylenically unsaturated monomer, more preferably 0.00001 to 0.01 mol, further preferably 0.00001 to 0.005 mol and further more preferably 0.00005 to 0.002 mol.

[Azo Based Compound and Peroxide]

In the method of producing a water-absorbent resin according to the present invention, the phrase "in the presence of an azo based compound and a peroxide" does not necessarily means that the azo based compound and the peroxide are coexistent at the beginning of a polymerization reaction, but means that one compound is present before a monomer conversion ratio by radical cleavage due to the other compound becomes 10% or more. However, the both are preferably present in an aqueous solution containing a monomer before the start of the polymerization reaction. Further, an azo based compound and a peroxide may be added to a polymerization reaction system via different flow channels or may be sequentially added to the polymerization reaction system via the same flow channel. Note that an azo based compound and a peroxide to be used may be in the form of powder or an aqueous solution.

(Azo Based Compound)

Azo based compounds include, for example, those azo based compounds such as 1-{(1-cyano-1-methylethyl)azo}formamide, 2,2'-azobis[2-(N-phenyl amidino)propane]dihydrochloride, 2,2'-azobis{2-[N-(4-chlorophenyl)amidino]propane}dihydrochloride, 2,2'-azobis{2-[N-(4-hydroxyphenyl)amidino]propane}dihydrochloride, 2,2'-azobis[2-(N-benzyl amidino)propane]dihydrochloride, 2,2'-azobis[2-(N-allyl amidino)propane]dihydrochloride, 2,2'-azobis(2-amidinopropane)dihydrochloride, 2,2'-azobis{2-[N-(2-hydroxyethyl)amidino]propane}dihydrochloride, 2,2'-azobis[2-(5-methyl-2-imidazoline-2-yl)propane]dihydrochloride, 2,2'-azobis[2-(2-imidazoline-2-yl)propane]dihydrochloride, 2,2'-azobis[2-(4,5,6,7-tetrahydro-1H-1,3-diazepine-2-yl)propane]dihydrochloride, 2,2'-azobis[2-(5-hydroxy-3,4,5,6-tetrahydro-pyrimidine-2-yl)propane]dihydrochloride, 2,2'-azobis{2-[1-(2-hydroxyethyl)-2-imidazoline-2-yl]propane}dihydrochloride, 2,2'-azobis[2-(2-imidazoline-2-yl)propane], 2,2'-azobis{2-methyl-N-[1,1-bis(hydroxymethyl)-2-hydroxyethyl]propionamide}, 2,2'-azobis{2-methyl-N-[1,1-bis(hydroxymethyl)ethyl]propionamide}, 2,2'-azobis[2-methyl-N-(2-hydroxyethyl)propionamide], 2,2'-azobis(2-methylpropionamide)dihydrochloride, 4,4'-azobis-4-cyanovaleinic acid, 2,2'-azobis[2-(hydroxymethyl)propionitrile], 2,2'-azobis[2-(2-imidazoline-2-yl)propane]disulfate dihydrate, 2,2'-azobis[N-(2-carboxyethyl)-2-methylpropione amidine]tetrahydrate, 2,2'-azobis[2-methyl-N-(2-hydroxyethyl)propionamide]. Among these, 2,2'-azobis(2-amidinopropane)dihydrochloride, 2,2'-azobis{2-[1-(2-hydroxyethyl)-2-imidazoline-2-yl]propane}dihydrochloride, 2,2'-azobis[N-(2-carboxyethyl)-2-methylpropione amidine] tetrahydrate are preferred. These azo based compounds may be used alone or in combination of two or more.

(Peroxide)

Peroxides include, for example, persulfates such as potassium persulfate, ammonium persulfate, sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxy isobutyrate, t-butyl peroxy pivalate, hydrogen peroxide. Among these peroxides, potassium persulfate, ammonium persulfate, sodium persulfate, hydrogen peroxide are preferably used, and further, potassium persulfate, ammonium persulfate, sodium persulfate are more preferably used. These peroxides may be used alone or in combination of two or more.

(Used Amount and Used Proportion of Azo Based Compound and Peroxide)

The used amount of an azo based compound and a peroxide is preferably 0.00005 mol or more relative to 1 mol of a water soluble ethylenically unsaturated monomer, more preferably 0.0001 mol or more. Further, the used amount is preferably 0.005 mol or less relative to 1 mol of a water-soluble ethylenically unsaturated monomer, and more preferably 0.001 mol or less.

For the used proportion of an azo based compound and a peroxide, the proportion of the azo based compound is preferably 40 mass % or more relative to the total used amount of the azo based compound and the peroxide, more preferably 50 mass % or more, further preferably 60 mass % or more and further more preferably 70 mass %. On the other hand, the proportion of an azo based compound is preferably 95 mass % or less relative to the total used amount of the azo based compound and the peroxide, more preferably 90 mass % or less, further preferably 85 mass % and further more preferably 80 mass % or less. Further, the range of the mass ratio (azo based compound:peroxide) is preferably 8:12 to 19:1.

[Other Components]

In the method of producing a water-absorbent resin according to the present invention, other components may be added to a water-soluble ethylenically unsaturated monomer to perform reversed phase suspension polymerization, if desired. As other components, chain transfer agents, thickeners, other various additives and the like may be added.

(Chain Transfer Agent)

For example, a water-soluble ethylenically unsaturated monomer may be polymerized in the presence of a chain transfer agent in order to control the water-absorption performance of the water-absorbent resin.

Chain transfer agents include, for example, thiols such as ethanethiol, propanethiol, dodecanethiol; thiolic acids such as thioglycolic acid, thiomalic acid, dimethyldithiocarbamic acid, diethyldithiocarbamic acid or salts thereof; secondary alcohols such as isopropanol; phosphorous acid compounds, for example, phosphorous acid, normal salts of phosphorous acid such as disodium phosphite, dipotassium phosphite, diammonium phosphite, acid salts of phosphorous acid such as sodium hydrogen phosphite, potassium hydrogen phosphite, ammonium hydrogen phosphite, and the like; phosphoric acid compound, for example, phosphoric acid, normal salts of phosphoric acid such as sodium phosphate, potassium phosphate, ammonium phosphate, acid salts of phosphoric acid such as sodium dihydrogen phosphate, potassium dihydrogen phosphate, ammonium dihydrogen phosphate, disodium hydrogen phosphate, dipotassium hydrogen phosphate, diammonium hydrogen phosphate, and the like; hypophosphorous acid compounds, for example, hypophosphorous acid, hypophosphites such as sodium hypophosphite, potassium phosphinate, ammonium hypophosphorous; pyrophosphoric acid, tripolyphosphoric acid, polyphosphoric acid and salts thereof; trimethyl phosphate, nitrilo trimethylene triphosphonic acid and the like. These chain transfer agents may be used alone or in combination of two or more. Further, chain transfer agents may be used as hydrates thereof.

The used amount of a chain transfer agent is preferably 0.00001 to 0.0005 mol relative to 1 mol of a water-soluble ethylenically unsaturated monomers, more preferably 0.000025 to 0.00012 mol.

(Thickener)

Further, a thickener may be added to an aqueous solution containing a water-soluble ethylenically unsaturated monomer to perform reversed phase suspension polymerization. By adding a thickener to adjust the viscosity of an aqueous solution as described above, the median particle diameter obtained by reversed phase suspension polymerization may also be controlled.

As a thickener, for example, hydroxyethyl cellulose, hydroxypropyl cellulose, methyl cellulose, carboxymethyl cellulose, polyacrylic acid, (partially) neutralized polyacrylic acid, polyethylene glycol, polyacrylamide, polyethyleneimine, dextrin, sodium alginate, polyvinyl alcohol, polyvinyl pyrrolidone, polyethylene oxide and the like can be used. Note that the following tends to be observed: in a case where the stirring speeds at the time of polymerization are the same, the higher is the viscosity of an aqueous solution of a water-soluble ethylenically unsaturated monomer, the larger is the median particle diameter of the resulting particles.

[Reversed Phase Suspension Polymerization]

When performing reversed phase suspension polymerization, an aqueous monomer solution containing a water-soluble ethylenically unsaturated monomer is dispersed in a hydrocarbon dispersion medium, for example, in the presence of a dispersion stabilizer. When doing this, a dispersion stabilizer (a surfactant and/or a polymeric dispersion agent) may be added either before or after the aqueous monomer solution is dispersed as long as they are added before the start of a polymerization reaction.

In particular, in a view of easy reduction of the amount of a residual hydrocarbon dispersion medium in the resulting water-absorbent resin, it is preferred that polymerization is performed after an aqueous monomer solution is dispersed in a hydrocarbon dispersion medium in which a polymeric dispersion agent has been dispersed, and then a surfactant is further dispersed.

In the method of producing a water-absorbent resin according to the present invention, reversed phase suspension polymerization can be performed as described above in a single step or multiple steps such as two or more steps. Further, in view of increasing productivity, it is more preferably performed in 2 to 3 steps.

In a case where reversed phase suspension polymerization is performed in multiple steps such as two or more steps, after the first-step reversed phase suspension polymerization is performed, a water-soluble ethylenically unsaturated monomer may be added to the reaction mixture obtained in the first-step polymerization reaction, and mixed to perform a second-step reversed phase suspension polymerization as in the first step. In a case of reversed phase suspension polymerization at each step of the second step and later steps, reversed phase suspension polymerization is preferably performed by adding, in addition to a water-soluble ethylenically unsaturated monomer, an internal-crosslinking agent, an azo compound and a peroxide described above within the aforementioned range of the molar ratio of each component relative to the water-soluble ethylenically unsaturated monomer on the basis of the amount of the water-soluble ethylenically unsaturated monomer to be added in the reversed phase suspension polymerization in each step of the second step and later steps. Note that in the method of producing a water-absorbent resin according to the present invention, polymerization is also preferably performed in the presence of an azo based compound and a peroxide in polymerization of the second step and later steps.

The reaction temperature for a polymerization reaction is preferably 20 to 110° C., more preferably 40 to 90° C. from the viewpoint that economy may be improved by allowing rapid progress of a polymerization to reduce a polymerization time, and polymerization heat may be easily removed to perform a smooth reaction. Further, the reaction time is preferably 0.5 to 4 hours.

<Post-Crosslinking Step>

Next, in the method of producing a water-absorbent resin according to the present invention, post-crosslinking of a hydrous gel-like material obtained by polymerizing a water soluble ethylenically unsaturated monomer which has an internal-crosslinking structure is performed using a post-crosslinking agent (post-crosslinking reaction). This post-crosslinking reaction is preferably performed in the presence of a post-crosslinking agent after the polymerization of a water soluble ethylenically unsaturated monomer. By performing a post-crosslinking reaction of a hydrous gel-like material having an internal-crosslinking structure after the polymerization to increase a crosslinking density near a surface of a water-absorbent resin as described above, a water-absorbent resin can be obtained which has various enhanced properties such as a water-absorption capacity under a load and a water-absorption rate.

Post-crosslinking agents can include those compounds having two or more reactive functional groups. They include, for example, polyols such as ethylene glycol, propylene glycol, 1,4-butanediol, trimethylolpropane, glycerin, polyoxyethylene glycol, polyoxypropylene glycol, polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, (poly)glycerol polyglycidyl ether; haloepoxy compounds such as epichlorohydrin, epibromhydrin, α-methyl epichlorohydrin; isocyanate compounds such as 2,4-tolylene diisocyanate, hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol; oxazoline compounds such as 1,2-ethylenebisoxazoline; carbonate compounds such as ethylene carbonate; hydroxyalkylamide compounds such as bis[N,N-di(β-hydroxyethyl)]adipamide. Among these post-crosslinking agents, preferred are polyglycidyl compounds such as (poly) ethylene glycol diglycidyl ether, (poly)glycerin diglycidyl ether, (poly)glycerol triglycidyl ether, trimethylolpropane triglycidyl ether, (poly)propylene glycol polyglycidyl ether, (poly)glycerol polyglycidyl ether. These post-crosslinking agents may be used alone or in combination of two or more.

The used amount of a post-crosslinking agent is preferably 0.00001 to 0.01 mol relative to 1 mol of the total amount of a water-soluble ethylenically unsaturated monomer used for polymerization, more preferably 0.00005 to 0.005 mol and further preferably 0.0001 to 0.002 mol.

As a method of adding a post-crosslinking agent, the post-crosslinking agent may be added as it is or as an aqueous solution. A post-crosslinking agent may also be added as a solution in which a hydrophilic organic solvent is used as a solvent, if desired. Hydrophilic organic solvents include, for example, lower alcohols such as methyl alcohol, ethyl alcohol, n-propyl alcohol, isopropyl alcohol; ketones such as acetone, methyl ethyl ketone; ethers such as diethyl ether, dioxane, tetrahydrofuran; amides such as N,N-dimethylformamide; sulfoxides such as dimethyl sulfoxide. These hydrophilic organic solvents may be used alone or in combination of two or more, or may be used as a mixed solvent with water.

A post-crosslinking agent may be added after the polymerization reaction of water-soluble ethylenically unsaturated monomer has been almost completed, and it is preferably added in the presence of water in the range of 1 to 400 parts by mass relative to 100 parts by mass of a water-soluble ethylenically unsaturated monomer, more preferably added in the presence of water in the range of 5 to 200 parts by mass, further preferably added in the presence of water in the range of 10 to 100 parts by mass and further more preferably added in the presence of water in the range of 20 to 60 parts by mass. Note that the amount of water means the total amount of a water content in a reaction system and a water content used if desired when adding a post-crosslinking agent.

The reaction temperature in the post-crosslinking reaction, but it is preferably 50 to 250° C., more preferably 60 to 180° C., further preferably 60 to 140° C. and further more preferably 70 to 120° C. Further, the reaction time for the post-crosslinking reaction is preferably for 1 to 300 minutes, and more preferably for 5 to 200 minutes.

<Drying Step>

The method of producing a water-absorbent resin according to the present invention may comprise a drying step of removing water, a hydrocarbon dispersion medium and the like using distillation by applying energy such as heat from the outside after performing the aforementioned reversed phase suspension polymerization. When performing dehydration of a hydrous gel after reversed phase suspension polymerization, a system in which the hydrous gel is dispersed in a hydrocarbon dispersion medium is heated to temporarily evaporate water and the hydrocarbon dispersion medium from the system by azeotropic distillation. At this time, only the hydrocarbon dispersion medium evaporated is allowed to return into the system, enabling continuous azeotropic distillation. In that case, the temperature in the system during the drying treatment is maintained at or below the azeotropic temperature with the hydrocarbon dispersion medium. Therefore this is preferred in view of that, for example, the resin is less susceptible to deterioration. Water and the hydrocarbon dispersion medium is continuously evaporated away to obtain particles of a water-absorbent resin. By controlling processing conditions of this drying step after polymerization to adjust the amount of dehydrated water, various properties of the resulting water-absorbent resin can be controlled.

In the drying step, the drying treatment may be performed by distillation under ordinary pressure or under a reduced pressure. Further, the drying treatment may be performed under a gas flow of nitrogen and the like in view of increased drying efficiency. When performing the drying treatment under ordinary pressure, a drying temperature is preferably 70 to 250° C., more preferably 80 to 180° C., further preferably 80 to 140° C. and further more preferably 90 to 130° C. Further, when performing the drying treatment under reduced pressure, a drying temperature is preferably 40 to 160° C., more preferably 50 to 110° C.

Note that in a case where post-crosslinking step is performed with a post-crosslinking agent after monomers are polymerized by reversed phase suspension polymerization, the drying step is performed by distillation as described above after the post-crosslinking step. Alternatively, the post-crosslinking step and the drying step may be performed simultaneously.

Further, if desired, various additives such as chelating agents, reducing agents, oxidizing agents, antibacterial agents, deodorizing agents may be added to a water-absorbent resin after polymerization, during or after drying.

2. Water-Absorbent Resin

Next, the water-absorbent resin according to the present invention will be described. The water-absorbent resin according to the present invention can be obtained by polymerizing a water-soluble ethylenically unsaturated monomer in the presence of an internal-crosslinking agent, and performing post-crosslinking with a post-crosslinking agent, and characterized by that the water-absorption capacity of physiological saline under a load of 4.14 kPa at 120 minutes passed from the start of water absorption is 20 ml/g or more.

For the water-absorbent resin according to the present invention, the water-absorption capacity of physiological saline under a load of 4.14 kPa at 120 minutes passed from the start of water absorption is 20 ml/g or more, preferably 22 ml/g or more, more preferably 24 ml/g, and further preferably 26 ml/g. Further the water-absorption capacity of physiological saline under a load of 4.14 kPa at 120 minutes passed from the start of water absorption is preferably 50 ml/g or less, and more preferably 40 ml/g or less.

Furthermore, the water-absorbent resin according to the present invention is characterized by that the degree of swelling under a load at 30 minutes is 70% or less. Note that the degree of swelling under a load after a certain time has passed means a proportion of [the water-absorption capacity of physiological saline under a load of 4.14 kPa after a certain time has passed (for example, after 30 minutes)] relative to [the water-absorption capacity of physiological saline under a load of 4.14 kPa at 120 minutes passed from the start of water absorption], and may be calculated by the following formula.

$$\text{Degree of swelling under a load at a certain time passed (\%)} = \frac{\text{Water absorption capacity for physiological saline under a load of 4.14 kPa at a certain time passed (ml/g)}}{\text{Water absorption capacity for physiological saline under a load of 4.14 kPa at 120 minutes passed (ml/g)}} \times 100 \quad \text{[Formula 2]}$$

A water-absorbent resin showing a degree of swelling under a load at 30 minutes of 70% or less means that it will slowly absorb a liquid (to-be-absorbed liquid) under a load over a long time period at a predetermined water-absorption capacity. The degree of swelling under a load at 30 minutes is preferably 65% or less, more preferably 60% or less, and further preferably 55% or less. On the other hand, the degree of swelling under a load at 30 minutes is preferably 15% or more, more preferably is 20% or more, and further preferably 25% or more, and further more preferably 30% or more.

Further, the degree of swelling under a load at 240 minutes is preferably 110% or more in order to further enhance effects when used for an absorbent material.

Further, for the water-absorbent resin according to the present invention, the water-retention capacity of physiological saline after 120 minutes is preferably 30 to 60 g/g, more preferably 35 to 55 g/g, further preferably 37 to 53 g/g and further more preferably 40 to 50 g/g. Note that a water-retention capacity of physiological saline represents a degree of a liquid absorption capacity of a water-absorbent resin per unit mass.

Moreover, for the water-absorbent resin according to the present invention, the water-retention degree of swelling after 15 minutes is preferably less than 95%. Here, the water-retention degree of swelling after a certain time has passed is a proportion of particles of [the water-retention capacity of physiological saline after a certain time has passed (for example, after 15 minutes)] relative to [the water-retention capacity of physiological saline after 120 minutes], and may be calculated by the following formula.

$$\text{Water-retention degree of swelling at a certain time passed (\%)} = \frac{\text{Water-retention capacity for physiological saline at a certain time passed (g/g)}}{\text{Water-retention capacity for physiological saline at 120 minutes passed (g/g)}} \times 100 \quad \text{[Formula 3]}$$

Further, the water-absorbent resin according to the present invention preferably has a median particle diameter of 200 to 600 µm, more preferably 250 to 500 µm, further preferably 300 to 450 µm and further more preferably 300 to 400 µm.

Further, in the water-absorbent resin according to the present invention, the mass proportion of particles from 150 to 850 µm relative to the whole proportion is preferably 85 mass % or more, and more preferably 90 mass % or more. Further, the mass proportion of particles from 300 to 400 µm relative to the whole proportion is preferably 20 mass % or more, more preferably 25 mass % or more, and further preferably 30 mass % or more.

Note that particles of water-absorbent resin may be in a form where each comprises a single particle, or may be in a form where fine particles (primary particles) are agglomerated (secondary particles). Forms of the primary particles include a substantially spherical form, an irregular fractured form, a plate-like form and the like. When primary particles are manufactured by reversed phase suspension polymerization, they include a substantially spherical single particle form having a smooth surface such as a true spherical shape, an elliptically spherical shape. Then, the flowability as powder is high because primary particles in such forms have a smooth surface. Further, agglomerated particles are not easily destroyed upon impact, and thus a water-absorbent resin having high particle strength can be formed because agglomerated particles tend to be more densely packed.

The water-retention capacity of physiological saline, the water-absorption capacity of physiological saline under a load of 4.14 kPa and the median particle diameter of the aforementioned water-absorbent resin can either be evaluated by the evaluation test methods described in Examples below.

Note that an additive may be blended depending on the purposes in order to provide various preferred properties on the resulting water-absorbent resin. Such additives include inorganic powders, surfactants, oxidizing agents, reducing agents, metal chelating agents, radical chain inhibitors, anti-oxidizing agents, antibacterial agents, deodorizing agents and the like. For example, the flowability of a water-absorbent resin can be improved by adding 0.05 to 5 parts by mass of amorphous silica as an inorganic powder relative to 100 parts by mass of the water-absorbent resin.

3. Absorbent Material and Absorbent Article

The water-absorbent resin according to the present invention may form an absorbent material for use in, for example, hygienic materials such as sanitary goods and disposable diapers, and may suitably be used in absorbent articles comprising absorbent materials.

Here, an absorbent material in which a water-absorbent resin is used comprises, for example, the water-absorbent resin and a hydrophilic fiber. The structures of the absorbent material include a dispersion mixture obtained by mixing a water-absorbent resin and a hydrophilic fiber to give a uniform composition, a sandwich structure in which a water-absorbent resin is sandwiched between layered hydrophilic fibers, a structure in which a water-absorbent resin and a hydrophilic fiber is wrapped in tissue, and the like. Note that other components, for example, adhesive binder such as thermal adhesive synthetic fibers, hot melt adhesives, adhesive emulsions for increasing the shape retention capability of an absorbent material may be included in the absorbent material.

The content of a water-absorbent resin in an absorbent material is preferably 5 to 95 mass %, more preferably 20 to 90 mass % and further preferably 30 to 80 mass %.

Hydrophilic fibers include cellulose fibers prepared from wood such as cotton-like pulp, mechanical pulp, chemical pulp, semi-chemical pulp; artificial cellulose fibers such as rayon, acetate; fibers comprising synthetic resin such as hydrophilized polyamide, polyester and polyolefine.

Moreover, an absorbent material in which a water-absorbent resin is used can be held between a liquid permeable sheet (a top sheet) through which a liquid can permeate and a liquid impermeable sheet (a back sheet) through which a liquid cannot permeate to give an absorbent article. The liquid permeable sheet is arranged on the side to be in contact with the body while the liquid impermeable sheet is arranged opposite to the side to be in contact with the body.

Liquid permeable sheets include nonwoven of an air through type, a span bond type, a chemical bond type, a needle punch type and the like comprising fiber such as polyethylene, polypropylene, polyester, etc. and porous synthetic resin sheets and the like. Further, liquid impermeable sheets include synthetic resin films comprising a resin such as polyethylene, polypropylene, polyvinyl chloride and the like.

EXAMPLES

4. Example

Hereafter, the present invention will be described in detail with reference to Examples and Comparative Examples. However, the present invention shall not in any way be limited to the following Examples and the like.

4-1. Method for Evaluation Test

[Evaluation Test of Water-Absorbent Resin]

Water-absorbent resins obtained from Examples 1, 2 and 3 and Comparative Examples 1 and 2 below were subjected to various tests described below for evaluation. In the followings, each evaluation test method will be described.

(1) Water-Retention Capacity of Physiological Saline

A cotton bag (cotton broadcloth No. 60, horizontal 100 mm×vertical 200 mm) into which 2.0 g of a water-absorbent resin was weighed out was placed into a 500 mL beaker. To the cotton bag containing the water-absorbent resin, 500 g of 0.9 mass % aqueous sodium chloride (physiological saline) was poured in one portion so that lumps were not formed. The upper part of the cotton bag was then closed with a rubber band, and stood for a predetermined time to allow the water-absorbent resin to swell. When a predetermined time has passed, the cotton bag was dehydrated for 1 minute using a dehydrator (made by KOKUSAN Co., Ltd., Product number: H-122) configured such that the centrifugal force would be 167 G. Then the mass Wa (g) of the cotton bag containing swollen gel after dehydration was measured. Similar procedures were performed without adding a water-absorbent resin, and the empty mass Wb (g) of the wet cotton bag was measured, and a water-retention capacity was calculated by the following formula. Note that in this Example, the water-absorbent resin was allowed to swell for each standing time of 15 minutes, 30 minutes, 60 minutes, 120 minutes, and a water-retention capacity was measured after each standing time.

Water-retention capacity of physiological saline $(g/g)=[Wa-Wb]$ (g)/mass (g) of water-absorbent resin (2) Water-Absorption Capacity of Physiological Saline Under a Load of 4.14 kPa A water-absorption capacity of physiological saline under a load of 4.14 kPa of a water-absorbent resin was measured using a measurement apparatus X. A schematic arrangement of the measurement apparatus X is shown in FIG. 1.

Figure 1:
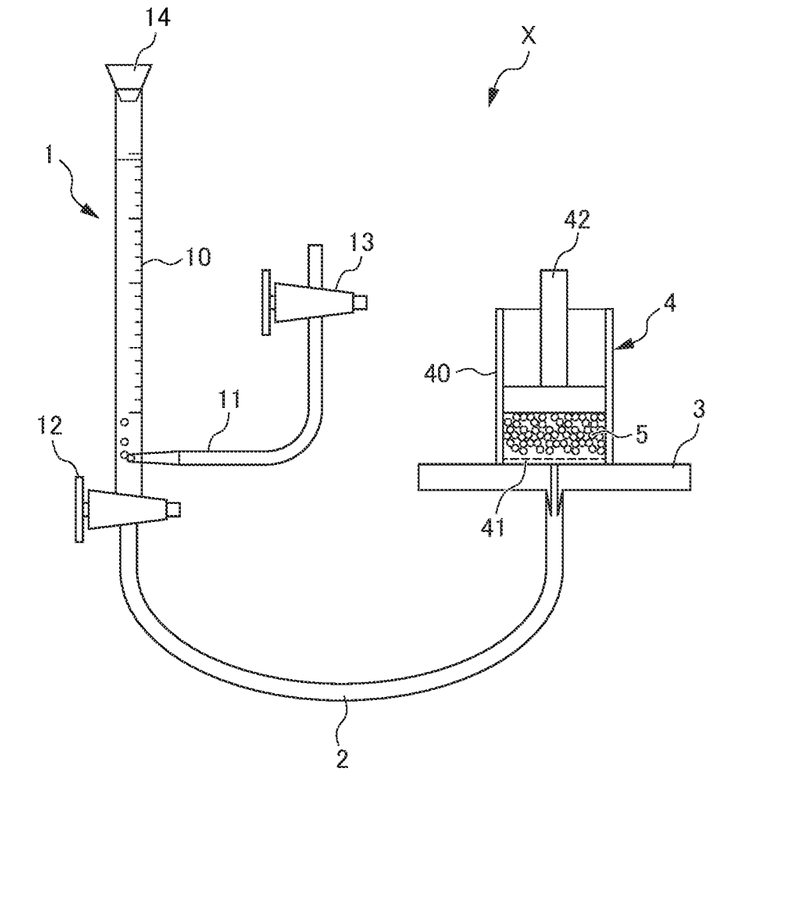
FIG. 1 shows a pattern diagram illustrating the schematic arrangement of an apparatus for measuring, in a water-absorbent resin, a water-absorption capacity of physiological saline under a load of 4.14 kPa.

The measurement apparatus X shown in FIG. 1 comprises a buret part 1, a conduit 2, a measurement stage 3, a measurement part 4 placed on the measurement stage 3. In the buret part 1, a rubber stopper 14 is connected to the upper part of a buret 10, and an air introducing pipe 11 and a cock 12 is connected to the lower part of the buret 10. Further, a cock 13 is attached to the upper part of the air introducing pipe 11. A conduit 2 connects the buret part 1 and the measurement stage 3. The diameter of the conduit 2 is 6 mm. The measurement stage 3 has a hole with a diameter of 2 mm at the center, to which the conduit 2 is connected. The measurement part 4 is provided with a cylinder 40 and a nylon mesh 41 patched on the bottom of the cylinder 40, as well as a weight 42. The inner diameter of the cylinder 40 is 2.0 cm. The nylon mesh 41 is formed as 200 mesh (75 µm openings). Further, it is configured such that a predetermined amount of a water-absorbent resin 5 is uniformly distributed on the nylon mesh 41. The weight 42 has a diameter of 1.9 cm and a mass of 119.6 g. The weight 42 is to be placed on the water-absorbent resin 5 to uniformly apply a load of 4.14 kPa to the water-absorbent resin 5.

Using the measurement apparatus X having a structure as described above, first, the cock 12 and the cock 13 at the buret part 1 were closed, and then physiological saline adjusted to 25° C. was introduced into the buret 10 from the top. Subsequently, the top of the buret was plugged with the rubber stopper 14, and then the cock 12 and the cock 13 at the buret part 1 were opened. Next, the height of the measurement stage 3 was adjusted so that the tip of the conduit 2 at the center of the measurement stage 3 is leveled with the air inlet of the air introducing pipe 11.

Meanwhile, 0.10 g of the water-absorbent resin 5 was uniformly distributed on the nylon mesh 41 in the cylinder 40, and then the weight 42 was placed on that water-absorbent resin 5. The measurement part 4 was arranged so that its center coincided with the conduit inlet at the center of the measurement stage 3.

The amount of reduced physiological saline in the buret 10 (the amount of physiological saline absorbed by the water-absorbent resin 5) We (mL) was continuously measured from the time point when the water-absorbent resin 5 started to absorb water. At each passing time of 30 minutes, 60 minutes, 120 minutes, and 240 minutes from the start of water absorption, a water-absorption capacity of physiological saline under a load of 4.14 kPa of the water-absorbent resin was calculated by the following formula.

Water-absorption capacity of physiological saline under a load of 4.14 kPa (mL/g)=$We/0.10$ (g)

(3) Median Particle Diameter (Particle Size Distribution)

JIS standard sieves were combined in the following order from the top: a sieve of 850 µm openings, a sieve of 600 µm openings, a sieve of 500 µm openings, a sieve of 400 µm openings, a sieve of 300 µm openings, a sieve of 250 µm openings, a sieve 150 µm openings and a receiving tray.

A water-absorbent resin in an amount of 50 g was introduced on the top of the combined sieves, and then shaken for 20 minutes using a ro-tap shaker for classification. After classification, the mass of the water-absorbent resin which remained in each sieve was calculated as a mass proportion of particles relative to the total mass to obtain a particle size distribution. By integrating the amount on each sieve from the one having the largest particle diameter in this particle size distribution, the relationship between the sieve openings and the integrated value of the mass proportion of particles of the water-absorbent resin which remained in the sieves was plotted on logarithmic probability paper. By connecting the plots on the probability paper with a straight line, a particle diameter corresponding to 50 mass % in the integrated mass proportion of particles is taken as the median particle diameter.

Note that the mass proportion of particles from 300 to 400 µm in the total water-absorbent resin is a mass proportion of particles of a water-absorbent resin which remained in the sieve with 300 µm openings relative to the whole proportion in the aforementioned measurements. Similarly, the mass proportion of particles from 150 to 850 µm in the total water-absorbent resin is a value obtained by summing the mass proportion of particles of the water-absorbent resin which remained in sieves with openings of 150 µm, 250 µm, 300 µm, 400 µm, 500 µm, and 600 µm.

[Evaluation Test of Absorbent Material and Absorbent Article in which Water-Absorbent Resin is Used]

(1) Production of Absorbent Material and Absorbent Article

Using 10 g of a water-absorbent resin and 10 g of crushed pulp (made by Rayonier, Rayfloc) were uniformly mixed by air papermaking to manufacture a sheet-like absorbent material core with a size of 40 cm×12 cm. Next, while the absorbent material core was placed between two tissue papers, which had the same size as the absorbent material core and a basis weight of 16 g/m2, the absorbent material core was all over pressed with a load of 196 kPa for 30 seconds to prepare an absorber absorbent material. Further, the absorbent article was prepared by arranging a polyethylene-polypropylene air-through porous liquid permeable sheet on the upper surface of the absorbent material, the sheet having a basis weight of 22 g/m$^2$ and the same size as the absorbent material, and arranging a polyethylene impermeable sheet of the same size and the same basis weight on the lower surface of the absorbent material.

(2) Preparation of Test Liquid

An appropriate amount of distilled water was introduced into a 10 L container, and 60 g of sodium chloride, 1.8 g of calcium chloride dihydrate and 3.6 g of magnesium chloride hexahydrate were added and dissolved. Subsequently, 0.15 g of polyoxyethylene nonylphenyl ether was added, and additional distilled water was further added to give a total mass of 6000 g. Further, coloring was performed with a small amount of Blue No. 1 to prepare a test liquid.

(3) Permeation Time

First, the absorbent article was first placed on a horizontal stage. On the center portion of the absorbent article, a measurement apparatus incorporating a liquid pouring cylinder having an inside diameter of 3 cm was placed, and 50 mL of the test liquid was poured into the cylinder at a time and a stopwatch was used to measure the time until the test liquid was made to disappear completely, with the result that the time was assumed to be the first permeation time (in seconds).

Then, the cylinder described above was removed, the absorbent article was stored in the present state and both when 30 minutes had elapsed and when 60 minutes had elapsed since the start of the first round of the pouring of the test liquid, the measurement apparatus was used in the position as in the first round, and the same operation was performed, with the result that the second and third permeation times (in seconds) were measured.

The total time of the first to third rounds was assumed to be the total permeation time. It is said that as the permeation time is shorter, the absorbent article was more preferable.

(4) Amount of Re-Wet

At 120 minutes after the state of the first round of the pouring of the test liquid in the measurement of the permeation time described above, in the vicinity of the position on the absorbent article where the test liquid was poured, filter paper 10 cm square whose mass (Wd (g), about 50 g) was previously measured was put, and thereon, a weight having a bottom surface of 10 cm×10 cm and a mass of 5 kg was placed. The load was placed for 5 minutes, and the mass (We (g)) of the filter paper was measured, with the result that the increased mass was assumed to be the re-wet amount (g). It is said that as the re-wet amount was decreased, the absorbent article was more preferable.

Amount of re-wet (g)=$We-Wd$ (5) Diffusion Length

Within 5 minutes after the measurement of the re-wet amount described above, the dimension (cm) of spread of the absorbent article in the longitudinal direction into which the test liquid is penetrated was measured. Note that values below the decimal point were rounded off.

4-2. Examples and Comparative Example

Example 1

A 2 L cylindrical round-bottom separable flask with an inner diameter of 110 mm was prepared which was equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane was introduced as a hydrocarbon dispersion medium, and 0.74 g of maleic anhydride modified ethylene-propylene copolymer (made by Mitsui Chemicals, Inc., High Wax 1105A) as a polymeric dispersion agent was added, and heat-dissolved with stirring, and then cooled to 50° C.

Meanwhile, 92 g (1.02 mol) of 80 mass % aqueous solution of acrylic acid was introduced into a 500 mL Erlenmeyer flask, and 102.2 g of 30 mass % aqueous solution of sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.092 g (0.339 mmol) of 2,2'-azobis(2-amidinopropane)dihydrochloride as an azo based compound, 0.037 g (0.137 mmol) of potassium persulfate as a peroxide, 0.010 g (0.058 mmol) of ethylene glycol diglycidyl ether as an internal-crosslinking agent and 43.8 g of ion exchange water were added and dissolved to prepare an aqueous monomer solution.

Then the aqueous monomer solution prepared as described above was added to a separable flask, and stirred for 10 minutes. Then, 7.4 g of a surfactant solution in which 0.74 g of HLB3 sucrose stearic acid ester (made by Mitsubishi-Kagaku Foods Corporation, Ryoto sugar ester S-370) as a surfactant was heat-dissolved in 6.66 g of n-heptane was further added, and the atmosphere in the system was thoroughly replaced with nitrogen with stirring. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % solution of aqueous acrylic acid was introduced to another 500 mL Erlenmeyer flask, and 143.1 g of 30 mass % aqueous solution of sodium hydroxide was added dropwise while cooling from the outside to perform 75 mol % neutralization. Subsequently, 0.129 g (0.475 mmol) of 2,2'-azobis(2-amidinopropane)dihydrochloride as an azo based compound, 0.052 g (0.191 mmol) of potassium persulfate as a peroxide, 0.012 g (0.067 mmol) of ethylene glycol diglycidyl ether as an internal-crosslinking agent and 15.9 g of ion exchange water were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Then the flask was again immersed into a 70° C. water bath to raise temperature, and a second-step polymerization was performed for 30 minutes.

After the second-step polymerization, the reaction liquid was heated to 125° C. in an oil bath, and 239 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently, drying was performed by evaporating n-heptane, and then a dried resin was obtained. This dried resin was mixed with 0.3 mass % of amorphous silica (made by Evonik Degussa Japan, Inc., Carplex #80), and allowed to pass through a sieve with 1000 µm openings to obtain 231.2 g of a water-absorbent resin in a form of agglomerated spherical particles. This water-absorbent resin was evaluated in accordance with the various test methods as described above.

Note that for the water-absorbent resin obtained, the mass proportion of particles from 150 to 850 µm relative to the whole proportion was 92 mass %, and the mass proportion of particles from 300 to 400 µm relative to the whole proportion was 32 mass %.

Example 2

In Example 2, the same was performed as in Example 1 except that after the second-step polymerization, 236 g of water was removed from the system by refluxing n-heptane in azeotropic distillation of n-heptane and water. Thereby, obtained was 234.1 g of a water-absorbent resin having a different water-retention capacity from the water-absorbent resin obtained in Example 1. This water-absorbent resin was evaluated in accordance with the various test methods as described above.

Note that for the water-absorbent resin obtained, the mass proportion of particles from 150 to 850 µm relative to the whole proportion was 94 mass %, and the mass proportion of particles from 300 to 400 µm relative to the whole proportion was 36 mass %.

Example 3

In Example 3, the same was performed as in Example 1 except that the addition amount of an internal-crosslinking agent ethylene glycol diglycidyl ether to be dissolved in the first-step aqueous monomer solution was 0.020 g (0.116 mmol), and after the second-step polymerization, 254 g of water was removed from the system by refluxing n-heptane in azeotropic distillation of n-heptane and water. Thereby, obtained was 232.9 g of a water-absorbent resin which differed from the water-absorbent resin obtained in Example 1 in that a different internal-crosslinking agent was used. This water-absorbent resin way was evaluated in accordance with the various test methods as described above.

Note that for the water-absorbent resin obtained, the mass proportion of particles from 150 to 850 µm relative to the whole proportion was 95 mass %, and the mass proportion of particles from 300 to 400 µm relative to the whole proportion was 33 mass %.

Comparative Example 1

In Comparative Example 1, reversed phase suspension polymerization was performed using only a peroxide alone to produce a water-absorbent resin.

A 2 L cylindrical round-bottom separable flask with an inner diameter of 110 mm was prepared which was equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane as a hydrocarbon dispersion medium was introduced, and 0.74 g of maleic anhydride modified ethylene-propylene copolymer (made by Mitsui Chemicals, Inc., High Wax 1105A) as a polymeric dispersion agent was added, and heat-dissolved with stirring. Then it was cooled to 50° C.

Meanwhile, 92 g (1.02 mol) of 80 mass % aqueous solution of acrylic acid was introduced into a 500 mL Erlenmeyer flask, and 102.2 g of 30 mass % aqueous solution of sodium hydroxide was added dropwise while cooling from the outside to perform 75 mol % neutralization. Subsequently, 0.092 g of hydroxylethyl cellulose (made by Sumitomo Seika Chemicals Co., Ltd., HEC AW-15F) as a thickener, 0.074 g (0.274 mmol) of potassium persulfate as a peroxide, 0.010 g (0.058 mmol) of ethylene glycol diglycidyl ether as an internal-crosslinking agent and 43.8 g of ion exchange water were added and dissolved to prepare an aqueous monomer solution.

Then the aqueous monomer solution prepared as described above was added to a separable flask, and stirred for 10 minutes. Then, 7.4 g of a surfactant solution in which 0.74 g of HLB3 sucrose stearic acid ester (made by Mitsubishi-Kagaku Foods Corporation, Ryoto sugar ester S-370) as surfactant was heat-dissolved in 6.66 g of n-heptane was further added, and the atmosphere in the system was thoroughly replaced with nitrogen with stirring. Then, the flask was immersed into a 70° C. water bath to raise temperature, and a first-step polymerization was performed for 60 minutes to obtain a first-step polymerized slurry.

Meanwhile, 128.8 g (1.43 mol) of 80 mass % aqueous solution of acrylic acid was introduced to another 500 mL Erlenmeyer flask, and 143.1 g of 30 mass % aqueous solution of sodium hydroxide was added dropwise while cooling from the outside to perform 75 mol % neutralization. Then, 0.104 g (0.382 mmol) of potassium persulfate as a peroxide, 0.012 g (0.067 mmol) of ethylene glycol diglycidyl ether as an internal-crosslinking agent and 15.9 g of ion exchange water were added and dissolved to prepare a second-step aqueous monomer solution.

After cooling the system in the aforementioned separable flask to 25° C., all of the second-step aqueous monomer solution was added to the first-step polymerized slurry, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 257 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently, drying was performed by evaporating n-heptane to obtain a dried resin. This dried resin was mixed with 0.3 mass % of amorphous silica (made by Evonik Degussa Japan, Inc., Carplex #80), and allowed to pass through a sieve with 1000 µm openings to obtain 228.2 g of a water-absorbent resin in a form of agglomerated spherical particles. This water-absorbent resin was evaluated in accordance with the various test methods as described above.

Note that in the resulting water-absorbent resin, the mass proportion of particles from 150 to 850 µm relative to the whole proportion was 94 mass %, and the mass proportion of particles from 300 to 400 µm relative to the whole proportion was 33 mass %.

Comparative Example 2

In Comparative Example 2, after a predetermined monomer conversion ratio was achieved in the polymerization performed by adding an azo based compound, a peroxide was added to perform reversed phase suspension polymerization for production of a water-absorbent resin.

A 2 L cylindrical round-bottom separable flask with an inner diameter of 110 mm was prepared which was equipped with a reflux condenser, a dropping funnel, a nitrogen gas-introducing tube and stirrer having stirring blades compound of two sets of 4 inclined paddle blades with a blade diameter of 50 mm. To this flask, 300 g of n-heptane as a hydrocarbon dispersion medium was introduced and 0.74 g of maleic anhydride modified ethylene-propylene copolymer (made by Mitsui Chemicals, Inc., High Wax 1105A) as a polymeric dispersion agent was added, and heat-dissolved with stirring. Then it was cooled to 50° C.

Meanwhile, 184 g (2.04 mol) of 80 mass % aqueous acrylic acid to a 1000 mL Erlenmeyer flask, and 292.0 g of 21 mass % aqueous solution of sodium hydroxide was added dropwise while cooling from the outside to perform 75 mol % neutralization, and the resulting aqueous monomer solution was evenly aliquoted into two.

Subsequently, 0.092 g (0.339 mmol) of 2,2'-azobis(2-amidinopropane)dihydrochloride as an azo based compound, 0.010 g (0.058 mmol) of ethylene glycol diglycidyl ether as an internal-crosslinking agent, 0.184 g of hydroxyethyl cellulose (made by Sumitomo Seika Chemicals Co., Ltd., HEC AW-15F) as a thickener were added to one aqueous monomer solution, and dissolved to prepare a aqueous monomer solution.

Then the aqueous monomer solution prepared as described above was added to a separable flask, and stirred for 10 minutes. Then, 7.4 g of a surfactant solution in which 0.74 g of HLB3 sucrose stearic acid ester (made by Mitsubishi-Kagaku Foods Corporation, Ryoto sugar ester S-370) as a surfactant was heat-dissolved in 6.66 g of n-heptane was further added, and the atmosphere in the system was thoroughly replaced with nitrogen with stirring. Then, the flask was immersed into a 70° C. water bath to raise temperature, and then a first-step polymerization was performed for 60 minutes. The system after cooled to 25° C. was taken as the 50% monomer conversion ratio, and an aqueous solution in which 0.037 g (0.137 mmol) of potassium persulfate as a peroxide was dissolved in 1.23 g of ion exchange water was added.

As an internal-crosslinking agent, 0.010 g (0.058 mmol) of ethylene glycol diglycidyl ether was added to the other aqueous monomer solution, and dissolved to prepare a second-step aqueous monomer solution.

All of the second-step aqueous monomer solution was added to the first-step polymerized slurry after addition of aqueous solution of potassium persulfate, and the atmosphere in the system was thoroughly replaced with nitrogen. Subsequently, the flask was again immersed into a 70° C. water bath to raise temperature, and a second-step polymerization was performed for 30 minutes.

After the second-step polymerization, the reaction liquid was heated to 125° C. in an oil bath, and 237 g of water was removed from the system by refluxing n-heptane in azeotropic distillation of n-heptane and water. Then, 4.42 g (0.51 mmol) of 2 mass % aqueous solution of ethylene glycol diglycidyl ether was added as a post-crosslinking agent, and maintained at 80° C. for 2 hours. Subsequently, drying was performed by evaporating n-heptane to obtain a dried resin. This dried resin was mixed with 0.3 mass % of amorphous silica (Evonik Degussa Japan, Inc., Carplex #80), and allowed to pass through a sieve with 1000 μm openings to obtain 199.5 g of a water-absorbent resin in a form of agglomerated spherical particles. This water-absorbent resin was evaluated in accordance with the various test methods as described below.

Note that in the resulting water-absorbent resin, the mass proportion of particles from 150 to 850 μm relative to the whole proportion was 93 mass %, and the mass proportion of particles from 300 to 400 μm relative to the whole proportion was 28 mass %.

4-3. Evaluation Results

[Evaluation Results of Water-Absorbent Resin]

First, shown in Table 1 below are the water-retention capacities (measured values) of physiological saline after corresponding standing times when allowed to stand to absorb water for 15 minutes, 30 minutes, 60 minutes, and 120 minutes, and the water-retention degrees of swelling (%) which is calculated by the following formula based on the analytical value of its water-retention capacity when the water-retention capacity of a water-absorbent resin after 120 minutes (the 120-minute value) is taken as a water-retention degree of swelling of 100%. Note that also shown in Table 1 are evaluation results of the median particle diameter (μm) of each water-absorbent resin obtained in Examples and Comparative Examples.

$$\text{Water-retention degree of swelling at a certain time passed (\%)} = \frac{\text{Water-retention capacity for physiological saline at a certain time passed (g/g)}}{\text{Water-retention capacity for physiological saline at 120 minutes passed (g/g)}} \times 100 \quad [\text{Formula 4}]$$

TABLE 1

| | Water-retention capacity of physiological saline (Measured value) | | | | Degree of swelling at water-retention capacity (%) (When 120-minute value was taken as 100%) | | | | Median particle diameter (μm) |
|---|---|---|---|---|---|---|---|---|---|
| | Passing time (min.) | | | | | | | | |
| | 15 | 30 | 60 | 120 | 15 | 30 | 60 | 120 | |
| Example 1 | 40.4 | 46.0 | 46.7 | 47.8 | 84 | 96 | 98 | 100 | 342 |
| Example 2 | 36.0 | 40.3 | 41.0 | 41.7 | 86 | 97 | 98 | 100 | 333 |
| Example 3 | 38.2 | 39.4 | 40.0 | 40.2 | 95 | 98 | 99 | 100 | 372 |
| Comparative Example 1 | 39.8 | 40.1 | 40.4 | 40.5 | 98 | 99 | 100 | 100 | 360 |
| Comparative Example 2 | 45.2 | 46.3 | 47.2 | 47.3 | 96 | 98 | 100 | 100 | 324 |

Next, shown in Table 2 below are a water absorption capacities (measured values) of physiological saline under a load of 4.14 kPa of water-absorbent resins at passing times of 30 minutes, 60 minutes, 120 minutes, and 240 minute after the start of water absorption, and the degrees of swelling under a load (%) which is calculated by the following formula based on the measured value of the water-absorption capacity of physiological saline under the load when a value after 120 minutes (the 120-minute value) for a water-absorbent resin is taken as a degree of swelling under a load of 100%. Note that also shown in Table 2 are evaluation results of the median particle diameter (μm) of each water-absorbent resin obtained in Examples and Comparative Examples.

$$\text{Degree of swelling under a load at a certain time passed (\%)} = \frac{\text{Water absorption capacity for physiological saline under a load of 4.14 kPa at a certain time passed (ml/g)}}{\text{Water absorption capacity for physiological saline under a load of 4.14 kPa at 120 minutes passed (ml/g)}} \times 100$$

[Formula 5]

TABLE 2

|  | Water-absorption capacity of physiological saline under a load of 4.14 kPa (ml/g) (Measured value) Passing time (min.) |  |  |  |  | Degree of swelling under a load (%) (When 120-minute value was taken as 100%) |  |  |  |  | Median particle diameter (μm) |
|---|---|---|---|---|---|---|---|---|---|---|---|
|  | 30 | 60 | 120 | 180 | 240 | 30 | 60 | 120 | 180 | 240 |  |
| Example 1 | 14.0 | 20.0 | 27.0 | 30.0 | 33.0 | 52 | 74 | 100 | 111 | 122 | 342 |
| Example 2 | 15.0 | 24.0 | 26.9 | 29.5 | 30.5 | 56 | 89 | 100 | 110 | 113 | 333 |
| Example 3 | 15.0 | 19.0 | 22.4 | 24.5 | 25.0 | 67 | 85 | 100 | 109 | 112 | 372 |
| Comparative Example 1 | 11.4 | 15.0 | 19.2 | 20.3 | 23.0 | 59 | 78 | 100 | 106 | 120 | 360 |
| Comparative Example 2 | 20.0 | 23.5 | 26.8 | 27.0 | 28.0 | 75 | 88 | 100 | 101 | 104 | 324 |

[Evaluation Results of Absorbent Articles]

Next, shown in Table 3 below are evaluation results of the permeation time, the amount of re-wet, the diffusion length of test liquid for absorbent articles produced using the water-absorbent resins obtained from Examples 1 and 2 and Comparative Example 1 described above.

Note that in a case of Reference Examples to evaluate these absorbent articles, a water-absorbent resin was collected from a commercially available absorbent article, and then an absorbent article was produced in a similar way as described in the sections describing (1) the method of producing an absorbent material and an absorbent article, and the permeation time, the amount of re-wet, the diffusion length of test liquid were measured. For Reference Example 1, a water-absorbent resin collected from MamyPoko (made by Unicharm Corporation) was used, and for Reference Example 2, a water-absorbent resin collected from Refre Pull-on Pants (made by Livedo Corporation) was used.

TABLE 3

|  | Performance of water-absorbent resin |  |  | Absorbent article (Production results) |  |  | Evaluation results of absorbent articles |  |  |  |  |  |
|---|---|---|---|---|---|---|---|---|---|---|---|---|
|  | Water-retention capacity*1 (g/g) | Water-absorption capacity under a load*2 (ml/g) | Degree of swelling under load*3 (%) | Water-absorbent resin (g) | Pulp (g) | Thickness (mm) | Permeation time (s) |  |  |  | Amount of re-wet (g) | Diffusion length (cm) |
|  |  |  |  |  |  |  | First time | Second time | Third time | Total |  |  |
| Example 1 | 47.8 | 27.0 | 52 | 10 | 10 | 3 | 18 | 18 | 23 | 59 | 7.8 | 18 |
| Example 2 | 41.7 | 26.9 | 56 | 10 | 10 | 3 | 18 | 17 | 22 | 57 | 12.8 | 19 |
| Example 3 | 40.5 | 19.2 | 59 | 10 | 10 | 3 | 19 | 19 | 28 | 66 | 27.9 | 16 |

TABLE 3-continued

| | Performance of water-absorbent resin | | | Absorbent article (Production results) | | | Evaluation results of absorbent articles | | | | | |
|---|---|---|---|---|---|---|---|---|---|---|---|---|
| | Water-retention capacity*1 (g/g) | Water-absorption capacity under a load*2 (ml/g) | Degree of swelling under load*3 (%) | Water-absorbent resin (g) | Pulp (g) | Thickness (mm) | Permeation time (s) | | | | Amount of re-wet (g) | Diffusion length (cm) |
| | | | | | | | First time | Second time | Third time | Total | | |
| Reference Example 1 | 36.2 | 12.5 | 80 | 10 | 10 | 3 | 18 | 19 | 28 | 65 | 33.6 | 17 |
| Reference Example 2 | 42.0 | 16.5 | 93 | 10 | 10 | 3 | 19 | 21 | 27 | 67 | 31.8 | 16 |

*1 The water-retention capacity represents 120-minute values for the water-retention capacity of physiological saline as measured by the method described in "(1) water-retention capacity of physiological saline" in the method of evaluation tests.
*2 The water-absorption capacity under a load represents a 120-minute value of the water-absorption capacity of physiological saline under a load of 4.14 kPa as measured by the method described in "(2) water-absorption capacity of physiological saline under a load of 4.14 kPa" in the method of evaluation tests.
*3 The degree of swelling under a load was calculated from a 30-minute value of the water-absorption capacity of physiological saline under a load of 4.14 kPa as measured by the method described in "(2) Water-absorption capacity of physiological saline under a load of 4.14 kPa" in the method of evaluation tests.

EXPLANATION OF REFERENCE NUMERALS

X Measurement apparatus
1 Buret part
2 Conduit
3 Measurement stage
4 Measurement part
5 Water-absorbent resin

The invention claimed is:

1. A method of producing a water-absorbent resin by performing polymerization comprising a step of polymerizing a water-soluble ethylenically unsaturated monomer in the presence of an internal-crosslinking agent, and a step of performing post-crosslinking with a post-crosslinking agent, wherein
the step of polymerizing a water-soluble ethylenically unsaturated monomer comprises two or more polymerization steps;
all the polymerization steps are performed in the presence of both one or more azo based compounds and one or more peroxides so that the both are coexistent in the all steps;
in the each step of the two or more polymerization steps, a proportion of the one or more azo based compound used in the polymerization step is 40 mass % or more and 95 mass % or less relative to a total amount of the azo based compounds and the peroxides used in the polymerization step;
the obtained water-absorbent resin has a water-absorption capacity of physiological saline under a load of 4.14 kPa at 120 minutes passed from the start of water absorption of 20 ml/g or more;
the degree of swelling under a load at 30 minutes is 70% or less when the water-absorption capacity of physiological saline under a load of 4.14 kPa at 120 minutes passed from the start of water absorption is taken as a degree of swelling under a load of 100%; and
the degree of swelling under a load at a certain time passed is calculated by the following formula:

$$\text{Degree of swelling under a load at a certain time passed (\%)} = \frac{\text{Water absorption capacity for physiological saline under a load of 4.14 kPa at a certain time passed (ml/g)}}{\text{Water absorption capacity for physiological saline under a load of 4.14 kPa at 120 minutes passed (ml/g)}} \times 100.$$

2. A method of producing an absorbent article using an absorbent material comprising the water-absorbent resin produced by the method according to claim 1.

* * * * *